(12) United States Patent
Hansen et al.

(10) Patent No.: US 7,699,976 B2
(45) Date of Patent: Apr. 20, 2010

(54) UPFLOW BIOREACTOR WITH SEPTUM AND PRESSURE RELEASE MECHANISM

(75) Inventors: Conly L. Hansen, North Logan, UT (US); Carl S. Hansen, Garland, UT (US); Kevin Pack, North Logan, UT (US); John Milligan, North Logan, UT (US); Bradley C. Benefiel, Idaho Falls, ID (US); C. Wayne Tolman, Rupert, ID (US); Kenneth W. Tolman, Rupert, ID (US)

(73) Assignee: Utah State University, North Logan, UT (US)

( * ) Notice: Subject to any disclaimer, the term of this patent is extended or adjusted under 35 U.S.C. 154(b) by 728 days.

(21) Appl. No.: 11/548,764

(22) Filed: Oct. 12, 2006

(65) Prior Publication Data

US 2008/0169231 A1 Jul. 17, 2008

(51) Int. Cl.
*C02F 3/28* (2006.01)
(52) U.S. Cl. .................................. 210/90; 210/603
(58) Field of Classification Search .................. 210/90, 210/130, 132, 603
See application file for complete search history.

(56) References Cited

U.S. PATENT DOCUMENTS

| | | | |
|---|---|---|---|
| 2,889,929 A | 6/1959 | Kivell et al. ................ 210/194 |
| 3,622,009 A | 11/1971 | Bordner et al. ............. 210/528 |
| 3,705,648 A | 12/1972 | Arvanitakis et al. ......... 210/744 |
| 3,837,493 A | 9/1974 | Lin ............................. 210/197 |
| 3,965,013 A | 6/1976 | Jackson et al. .............. 210/519 |
| 4,003,398 A | 1/1977 | Duveau |
| 4,208,279 A | 6/1980 | Varani et al. ................ 210/613 |
| 4,302,329 A | 11/1981 | Pfferkorn et al. ............. 210/97 |
| 4,350,588 A | 9/1982 | Tsubota et al. .............. 210/208 |
| 5,441,634 A | 8/1995 | Edwards et al. ............. 210/194 |
| 5,507,946 A * | 4/1996 | Stearns ....................... 210/202 |
| 5,529,692 A | 6/1996 | Kubler et al. ............... 210/603 |
| 5,660,724 A | 8/1997 | Pollock |
| 5,747,311 A | 5/1998 | Jewell et al. ................ 435/176 |
| 5,798,043 A | 8/1998 | Khudenko et al. .......... 210/603 |
| 5,866,002 A | 2/1999 | Yates et al. ................. 210/601 |
| 6,911,149 B2 | 6/2005 | Hansen et al. .............. 210/603 |
| 2006/0060524 A1 | 3/2006 | Chynoweth et al. |
| 2006/0065593 A1 | 3/2006 | Hansen et al. |

* cited by examiner

*Primary Examiner*—Fred Prince

(57) ABSTRACT

An upflow bioreactor includes a vessel having an inlet and an outlet configured for upflow operation. A septum is positioned within the vessel and defines a lower chamber and an upper chamber. The septum includes an aperture that provides fluid communication between the upper chamber and lower chamber. The bioreactor also includes means for releasing pressure buildup in the lower chamber. In one configuration, the septum includes a releasable portion having an open position and a closed position. The releasable portion is configured to move to the open position in response to pressure buildup in the lower chamber. In the open position fluid communication between the lower chamber and the upper chamber is increased. Alternatively the lower chamber can include a pressure release line that is selectively actuated by pressure buildup. The pressure release mechanism can prevent the bioreactor from plugging and/or prevent catastrophic damage to the bioreactor caused by high pressures.

21 Claims, 6 Drawing Sheets

UPFLOW BIOREACTOR WITH SEPTUM AND PRESSURE RELEASE MECHANISM

GOVERNMENT INTERESTS

Work described herein has been supported, in part by a grant from the United States Department of Agriculture and United States Department of Energy, grant number 68-3A75-3-153. Therefore, the Government may have certain rights in this invention.

BACKGROUND OF THE INVENTION

1. The Field of the Invention

The present invention relates to upflow bioreactors for decomposing organic materials. More particularly, the present invention relates to pressure release mechanisms for upflow bioreactors that have an aperture that can become plugged.

2. The Related Technology

A bioreactor is a device that uses bacteria to promote the decomposition or "digestion" of organic waste material into simple organics and gaseous biogas products. Biogas is typically a mixture of methane, carbon dioxide, hydrogen sulfide, and other volatile organic compounds. If produced in sufficient quantities, the methane gas can be used as a fuel.

Anaerobic digestion in open storage vessels has historically been utilized in waste water management, especially in livestock production, to reduce or convert complex organic matter to a smaller volume. This method has proven to be economical by reducing the volume of waste handled and by volatilizing some metabolites into the atmosphere. Some disadvantages of the process include poor ability to keep the anaerobic digestion process in balance, resulting in the release of malodorous gases and inefficient, incomplete conversion of digested organic matter into biogas. The slow rate of digestion and the poor quality of methane gas yielded makes the economic recovery of methane gas generally infeasible in open storage vessels.

Many attempts have been made to decompose organic waste using closed vessels. One type of closed vessel reactor that has shown very high decomposition rates is the upflow anaerobic sludge blanket reactor. In this reactor, waste material is introduced into the bottom of the reactor and forced up through the vessel where it passes through a blanket of bacteria, which decomposes the organic material and produces biogas, which can be collected and used as a fuel.

To achieve high decomposition rates in an upflow bioreactor, the bacterial culture should be well established. One important advantage of an upflow bioreactor is that it can be operated continuously. Thus, once the bacterial culture is established, the high rate of digestion can be maintained for an extended period of time (e.g. months or even years).

Recently, an upflow reactor has been developed that induces formation of the bacterial culture on startup and maintains a thicker or more enriched bacterial culture during operation. These benefits are achieved by placing a septum near the top of the fluid level of the reactor. The septum causes suspended solids to settle out of the fluid nearing the top of the reactor. These solids settle back into the biomass where digestion continues. The solids that are retained by the septum often include bacteria. By retaining these solids in the digester, the septum maintains a better bacterial culture and facilitates more complete digestion. Upflow reactors with a septum are capable of significantly reduced digestion retention times.

One problem with using a septum in an upflow bioreactor is the increased chance of plugging. To allow the effluent to exit the digester, the septum has an aperture. The aperture constricts flow and is thus susceptible to plugging. If the aperture plugs, extremely high pressure can build in the lower chamber as the bacteria continue to produce biogas.

The size of the aperture significantly impacts whether the aperture will plug. Although a larger diameter aperture would reduce the incidence of plugging, an aperture with a diameter sufficiently large to prevent all plugging would significantly diminish the ability of the septum to retain suspended solids.

BRIEF SUMMARY OF THE INVENTION

The present invention is directed to an upflow bioreactor for decomposing organic materials to produce biogas. The bioreactors include a septum for improved digestion and a pressure release mechanism for releasing pressure buildup that can occur in the event that the bioreactor becomes plugged.

The bioreactors of the present invention include a vessel having an inlet for receiving an organic material and an outlet for expelling bioreactor effluent. A septum is positioned within the vessel and defines a lower chamber and an upper chamber. The lower chamber contains a biomass that includes bacteria suitable for decomposing an organic material.

The septum includes an aperture that provides fluid communication between the lower chamber and the upper chamber. Biogas and digested material exit the lower chamber into the upper chamber via the aperture. The septum includes a releasable portion that is movable between an open position and a closed position. The releasable portion is configured to move to the open position in response to pressure buildup in the lower chamber. Opening the releasable portion increases the area of the opening, which increases the fluid communication between the lower chamber and the upper chamber, thereby allowing potentially obstructing material to be ejected from the lower chamber and/or releasing pressure buildup in the lower chamber.

In an alternative embodiment, pressure buildup in the lower chamber is released through a tube that exits the lower chamber. The tube can be filled with a fluid to prevent the contents of the lower chamber from escaping during normal operation. If the aperture in the septum becomes obstructed, pressure that builds in the lower chamber forces the fluid out, which allows excess gasses and fluids to exit the digester without damaging the vessel structure.

In yet another alternative embodiment, a pressure gauge detects a buildup of pressure in the lower chamber and opens a valve to release the excess pressure.

The pressure relief mechanisms that may be incorporated into the bioreactors of the present invention are advantageously used in combination with the septum and aperture. The pressure relief mechanism allows the digester to be operated with greater fluid restriction through the aperture in the septum than would otherwise be possible. The restricted flow improves retention of solids and maximizes digester performance as compared to a digester without a pressure release mechanism and having a larger aperture to prevent blockage and damage to the reactor. In the event that the advantageously smaller and more restrictive aperture becomes plugged, the obstructing material can escape or the excess pressure can be released until the obstruction can be removed via the pressure release mechanism.

The use of the pressure release mechanism in combination with a septum is particularly advantageous because it allows the aperture to be sized for maximum digester performance while avoiding plugging that can occur with restricted flow.

These and other advantages and features of the present invention will become more fully apparent from the following description and appended claims as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which.

DETAILED DESCRIPTION OF EXEMPLARY EMBODIMENTS

I. Introduction

The upflow bioreactors of the present invention advantageously provide rapid decomposition of organic wastes with low to no instances of plugging. The bioreactors of the present invention include a septum that facilitates the retention of solids within the bioreactor and a pressure release mechanism that is actuated if excess pressure builds in the lower chamber of the bioreactor. The pressure release mechanism can prevent the bioreactor from plugging and/or prevent catastrophic damage to the bioreactor caused by high pressures.

II. Upflow Biorectors

Figure 1:
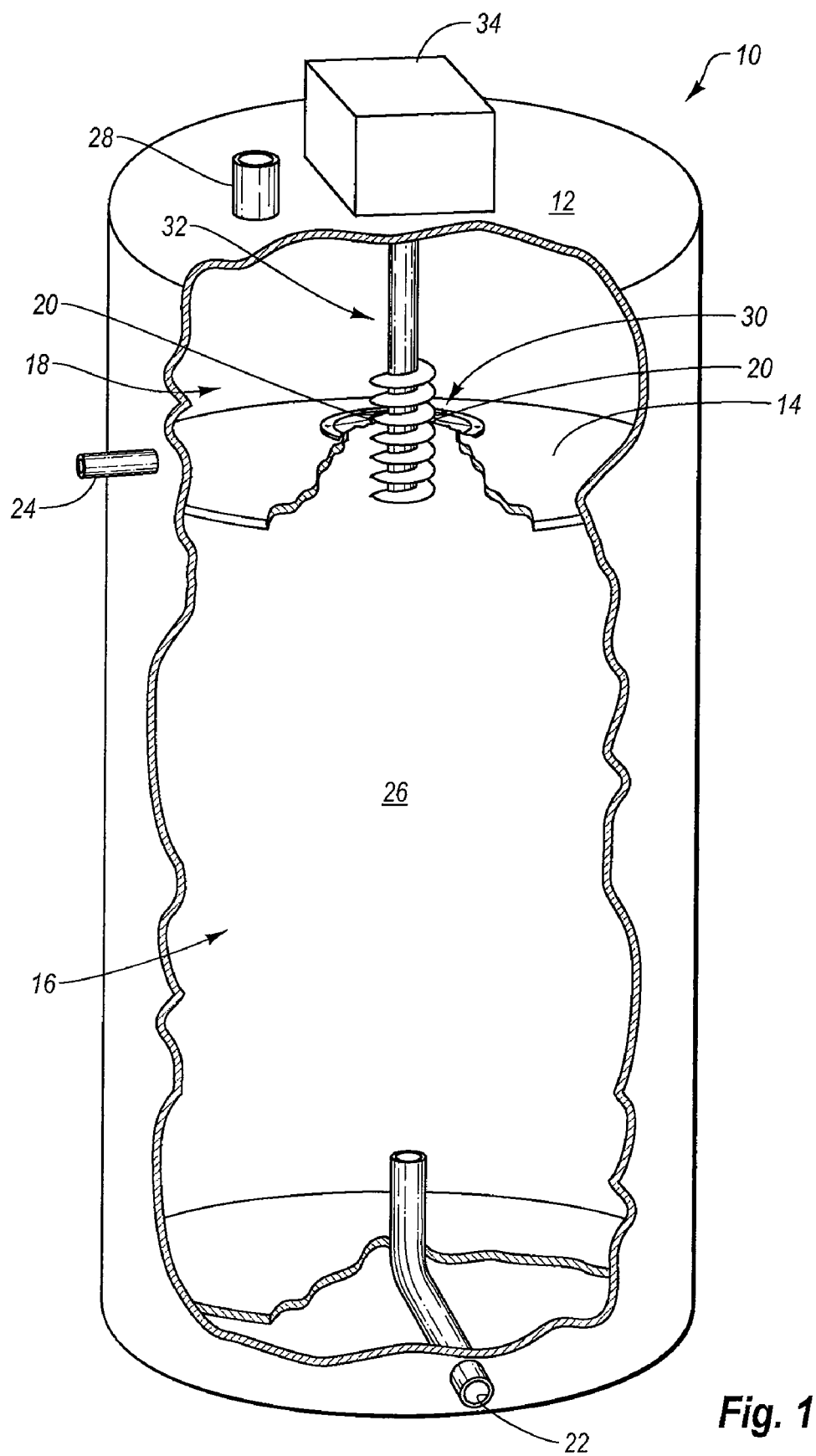
FIG. 1 illustrates an exemplary bioreactor according to the present invention with a portion of the bioreactor removed to show the interior components.

FIG. 1 illustrates an exemplary bioreactor 10 according to one embodiment of the present invention. Bioreactor 10 includes a vessel 12 in which an organic material (e.g. sewage) can be introduced and held for treatment. A septum 14 is positioned in vessel 12 to form a lower chamber 16 and an upper chamber 18. An aperture 20 in septum 14 provides fluid communication between lower chamber 16 and upper chamber 18. Septum 14 also includes a pressure release mechanism 30 that can release pressure buildup in lower chamber 16 by increasing the area of the opening of aperture 20. Bioreactor 10 optionally includes an auger 32 to facilitate the retention of solids suspended in the effluent passing through aperture 20. The auger can be driven by a drive assembly housed within housing 34.

Bioreactor 10 is configured for upflow operation. An inlet 22 is provided in lower chamber 16 for introducing organic material to be decomposed. A pump is typically coupled to inlet 22 to provide pressure for introducing the organic material. An outlet 24 is placed in upper chamber 18 to allow effluent to exit bioreactor 10. The placement of inlet 22 in lower chamber 16 and the placement of outlet 24 in upper chamber 18 creates an upflow in bioreactor 10 during operation. The upflow in bioreactor 10 can be continuous or semi-continuous.

Lower chamber 16 includes a biomass 26. Biomass 26 includes a microbial culture and organic material to be decomposed. The upflow in bioreactor 10 is sufficiently slow that a sludge blanket of bacteria can form in the biomass 26 of lower chamber 16. The organic material (e.g., animal waste) is slowly forced up through the sludge blanket where it is decomposed into smaller organic molecules and biogas. The microbial culture present in biomass 26 is selected according to the particular organic material that is to be decomposed in bioreactor 10. In an exemplary embodiment, the microbial culture comprises anaerobic bacteria. Anaerobic bacteria can be naturally occurring in some organic wastes (e.g. non-sterile animal manure).

Any organic material can be decomposed in bioreactor 10 so long as a microbial culture is available for degrading the organic material and the organic material can be introduced into the bioreactor in a form that can be mixed with the microbes. Examples of suitable organic materials that can be digested in the bioreactors of the present invention include animal wastes produced from the farming, ranching, and agricultural industries, food processing waste, human waste, and the like.

In a preferred embodiment, the type of microbial culture and type of organic material are selected such that the decomposition of the organic material produces biogas. Upper chamber 18 can be sealed such that biogas collects within upper chamber 18. A gas outlet 28 allows the biogas to be ported out of bioreactor 10. The biogas can advantageously be used as a fuel. For example, if desired, the biogas can be burned and the heat can be used to maintain an optimal operating temperature in bioreactor 10.

Figure 2:
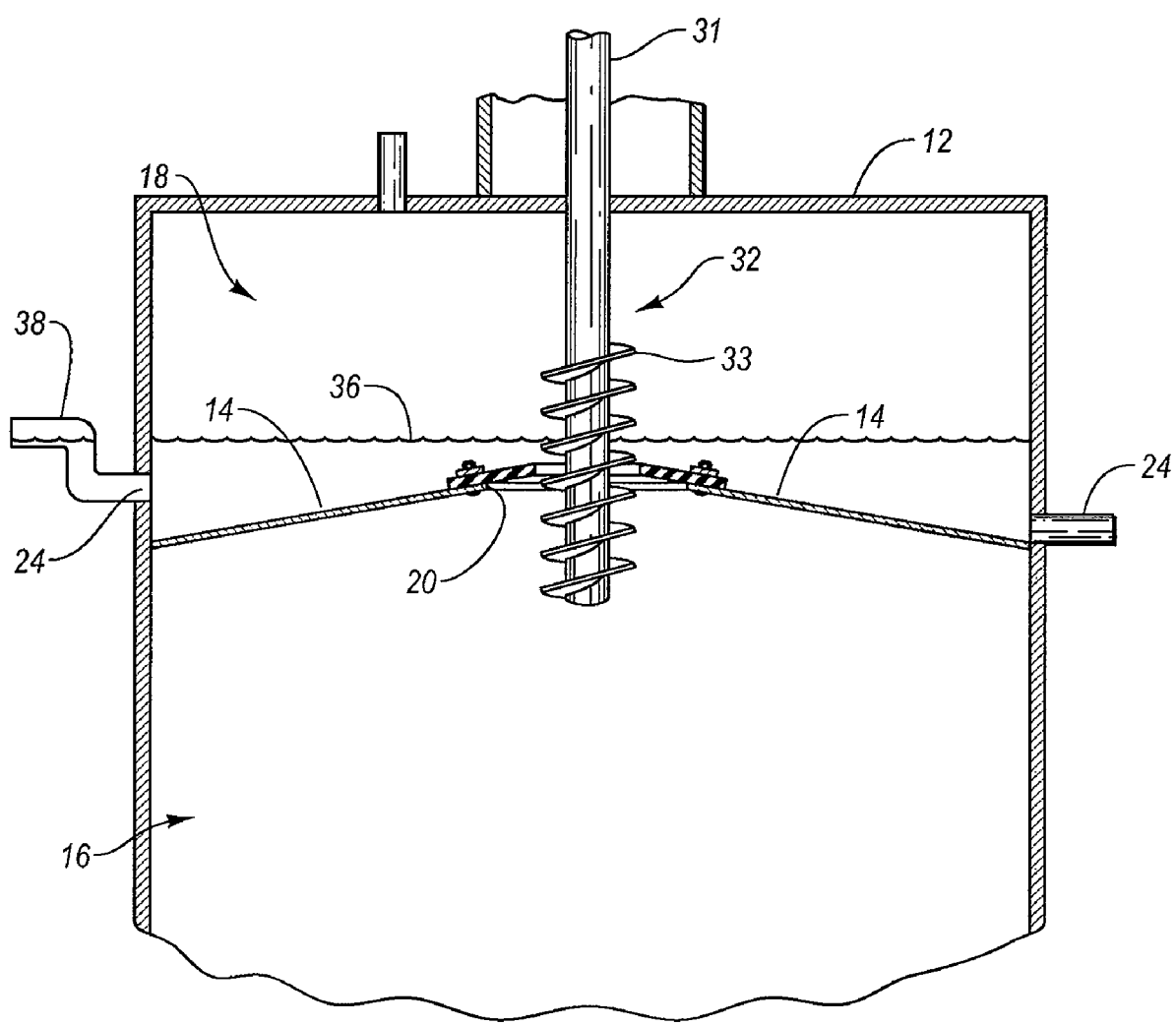
FIG. 2 is a cross-sectional view of a portion of the bioreactor of FIG. 1.

FIG. 2 shows a cross-section of a portion of bioreactor 10. The fluids within vessel 12 have a fluid level 36. Fluid level 36 is maintained by effluent outlet 24 and/or effluent line 38. Fluid level 36 is set below the top of vessel 12 such that a gas collection chamber is formed between the bioreactor fluids and the top of vessel 12.

Septum 14 is positioned within vessel 12 below fluid level 36. Septum 14 can be rigid or semi-rigid and can be made from any material compatible with the bioreactor fluids, including but not limited to plastics, metals, and the like. Septum 14 can be formed from a plurality of panels, or it can be a single, unitary piece of material. Septum 14 can be secured to the inside of the vessel 12 in any manner.

In an exemplary embodiment septum 14 slopes upwardly from the sidewalls of vessel 12 toward aperture 20. Sloping septum 14 can facilitate the removal of materials that settle out in upper chamber 18. A sloped septum can also be advantageous for ensuring that biogas in lower chamber 16 is directed to aperture 20. However, the present invention can also be carried out using a flat septum. In one embodiment, aperture 20 has a size and shape selected to minimize the escape of solids from the lower chamber and to minimize the incidence of the aperture becoming plugged by solids passing through the aperture.

In an exemplary embodiment, an auger 32 is operatively coupled to the enclosure 12 and positioned within aperture 20 of septum 14. Auger 32 can be any device that can be positioned within aperture 20 and can move solids in a desired direction between or within upper and lower chambers 16 and 18. In an exemplary embodiment, the auger includes a shaft with one or more flanges that are configured to move a material in a direction parallel to the shaft. Auger 32, shown in FIG. 2, includes a shaft 31 and a continuously spiraling flange 33.

When rotated clockwise, auger 32 creates a force that is opposite the flow of fluids in the bioreactor. During optimal or "normal" operating conditions, auger 32 is rotated in the direction that counters the flow of the bioreactor fluids. This counter-flow force tends to settle out solids suspended in the effluent passing through aperture 20. If aperture 20 becomes clogged, the auger 32 can be rotated in an opposite direction to remove solids to above the septum where the solids can be more easily cleaned out.

Auger 32 and septum 14 are provided to help form and maintain biomass 26. By retaining the bacteria within the lower chamber 16, septum 14 and auger 32 retain more bacteria, which are available for breaking down the organic material being fed into bioreactor 10. By utilizing the auger and septum, organic materials can be treated much faster and much more efficiently than organic waste being digested in other bioreactors. In addition, use of the septum and/or auger improves the clarity of effluent exiting the bioreactor.

Figure 3:
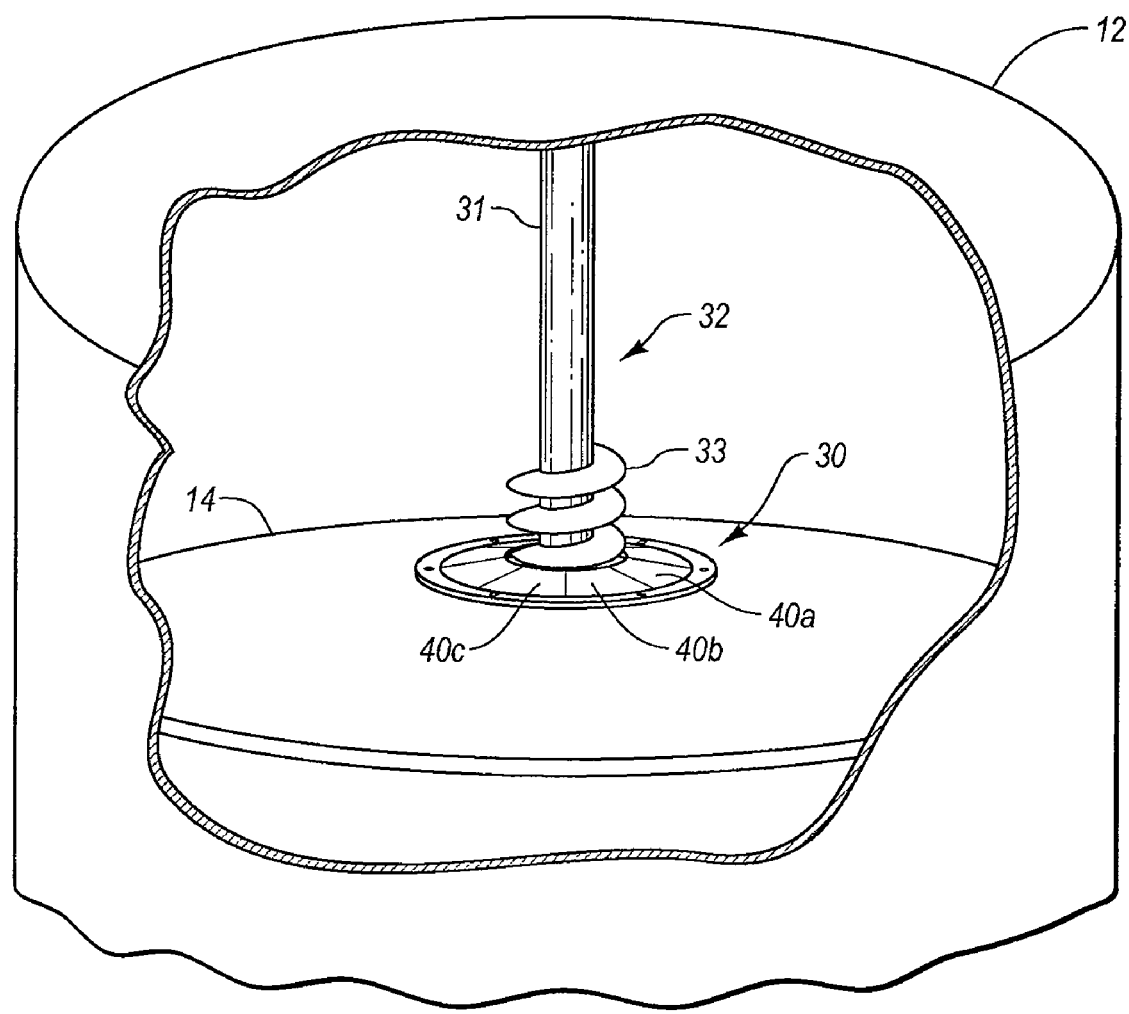
FIG. 3 is a perspective view of a portion of the bioreactor of FIG. 1.
Figure 4:
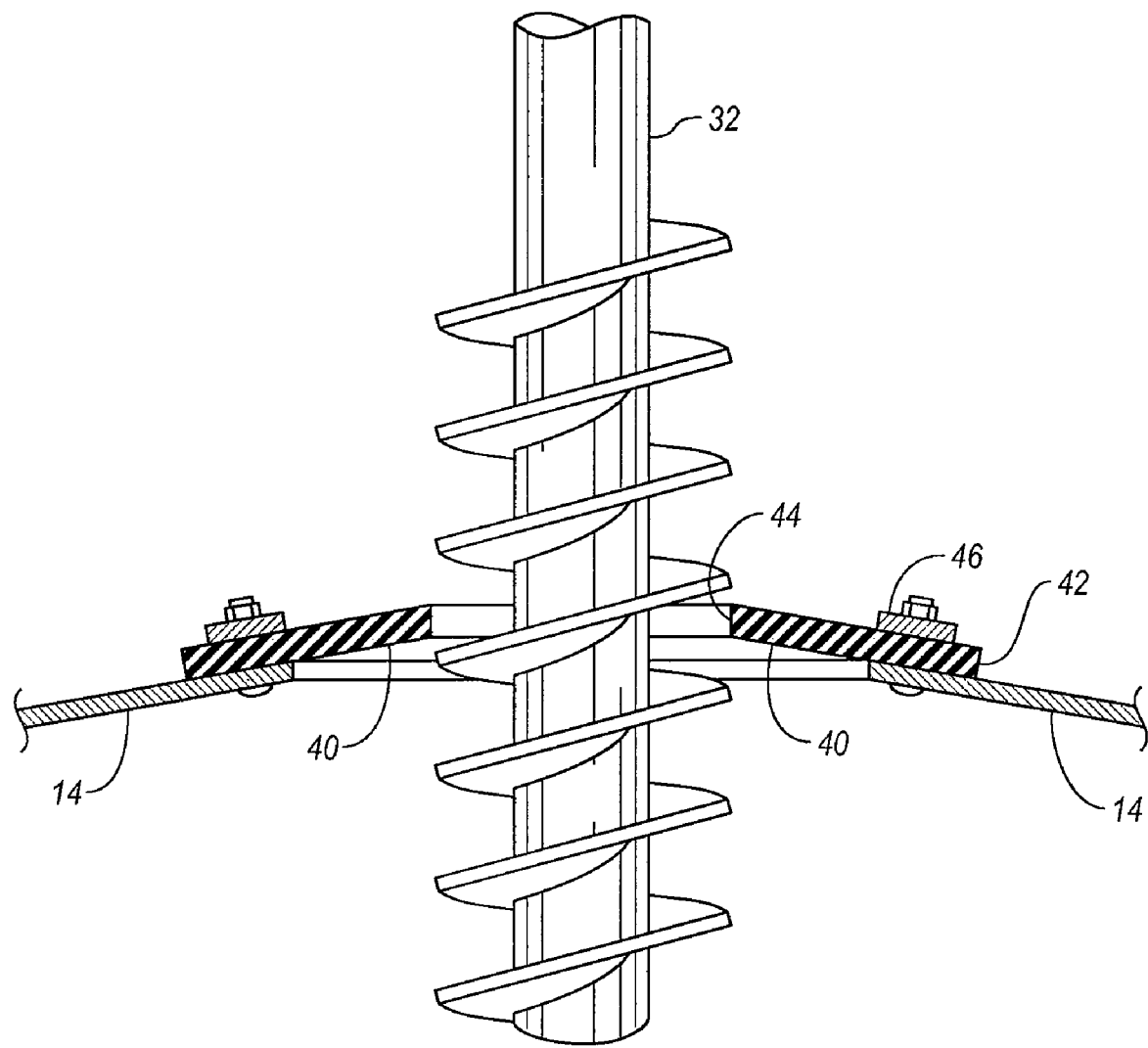
FIG. 4 is a cross-sectional view of the septum, pressure release mechanism, and auger of the bioreactor of FIG. 1.
Figure 5:
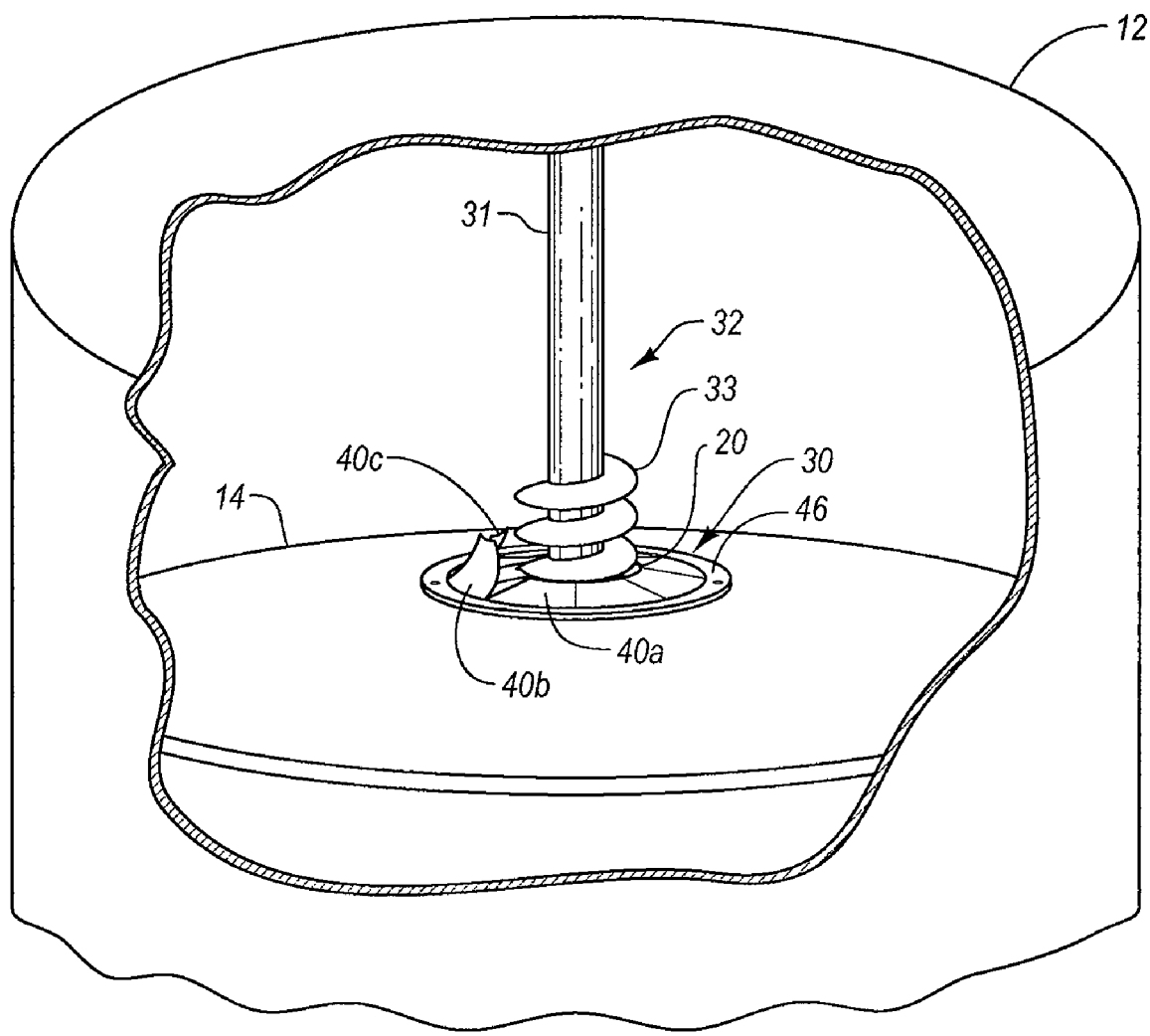
FIG. 5 is a perspective view of a portion of the bioreactor of FIG. 1 illustrating the open position of a portion of the pressure release mechanism.

To prevent plugging and/or pressure buildup in lower chamber 16, bioreactor 10 includes a pressure release mechanism. FIGS. 3-5 illustrate one embodiment of an exemplary pressure relief mechanism according to the present invention. FIG. 3 illustrates a pressure relief mechanism 30 that exemplifies a releasable portion of septum 14. Pressure relief mechanism 30 includes a plurality of flexible members (e.g., flexible members 40a, 40b, and 40c, collectively flexible members 40) that can flex in response to pressure buildup within lower chamber 16. As shown in FIG. 4, flexible members 40 are attached to the septum at a first end 42 and are free at a second end 44. In one embodiment, flexible members 40 are attached to septum 14 by a ring 46 and bolts 47. However, any attachment mechanism can be used so long as a portion of each flexible member is free to flex open.

Pressure release mechanism 30 allows septum 14 to have a variably sized aperture. When pressure release mechanism 30 is in a closed position aperture 20 has a first size. When pressure release mechanism 30 is in an open position, aperture 20 has a larger size, such that fluid communication between the upper and lower chambers is increased. Aperture 20 can be sized sufficiently large in the open position to allow material that would otherwise plug the aperture to pass through. In the closed position, flexible members 40 extend over a portion of the opening to reduce the fluid communication between the upper and lower chambers. So long as excess pressure does not build in lower chamber 16, effluent is forced around flexible members 40 and up through the aperture defined by the second edges (e.g. edge 44) of flexible members 40.

If pressure builds in lower chamber 16, flexible member 40 can be forced upward, thereby opening pressure release mechanism 30 and increasing the area of the aperture 20. The material that would otherwise plug the aperture is allowed to enter the upper chamber where it can be drawn out. FIG. 5 shows several flexible members flexed upward to increase the fluid communication between lower chamber 16 and upper chamber 18.

Flexible members 40 can be sized and configured to flex upward in response to a particular amount of pressure in lower chamber 16. Typically the dimensions of the flexible members, including length, width, and thickness can affect the force (i.e. pressure buildup) needed to actuate the flexible member. Thicker, stiffer materials tend to allow greater pressure to build before releasing. In one embodiment, the flexible members are rubber and/or have a thickness in a range from about 0.15 cm to about 1.5 cm.

The releasable portion of the septum and the aperture can be sized to provide almost any diameter of aperture while the pressure release mechanism 30 is in the open position. Examples of suitable aperture sizes for the open position can range from about 10 cm to about 2 meters, alternatively in a range from 20 cm to 100 cm. One benefit of a smaller aperture is that it can be less difficult to maintain the closed position while the pressure is below a selected level. However, larger sized apertures can still work if the releasable member is sufficiently rigid and/or if a suitable releasing mechanism is used.

The size of aperture 20 when the releasable portion is in the closed position can be selected to maximize solids retention. With the releasable portion closed, the size of the aperture is typically in a range from about 1 cm to about 20 cm, alternatively in a range from about 2 cm to about 10 cm. The preferred size of the aperture can depend on the type of material being digested, the size of the bioreactor, and the presence or absence of an auger.

In an alternative embodiment, the flexible member can be a single piece or can be sectioned into more or fewer pieces than pressure relief mechanism 30. The flexible member is also not necessarily flexible along its entire length, so long as a portion of the flexible member is sufficiently flexible to allow the flexible member to move to an open configuration.

Locating pressure relief mechanism 30 around auger 32 and aperture 20 can be advantageous since pressure buildup in lower chamber 16 can be released by allowing the material plugging aperture 20 to pass around auger 32. However, if desired, the releasable portion of septum 14 can be located away from aperture 20. In this embodiment, actuating a flexible member or other releasable portion can cause an entirely different aperture to open in the septum.

The present invention can be carried out using mechanisms other than a flexible member to increase the fluid communication between the upper chamber and lower chamber. For example, a portion of the septum can hingedly open in response to pressure. The foregoing mechanisms, including the flexible members described above, are examples of means for releasing pressure in the lower chamber of the bioreactor.

Figure 6:
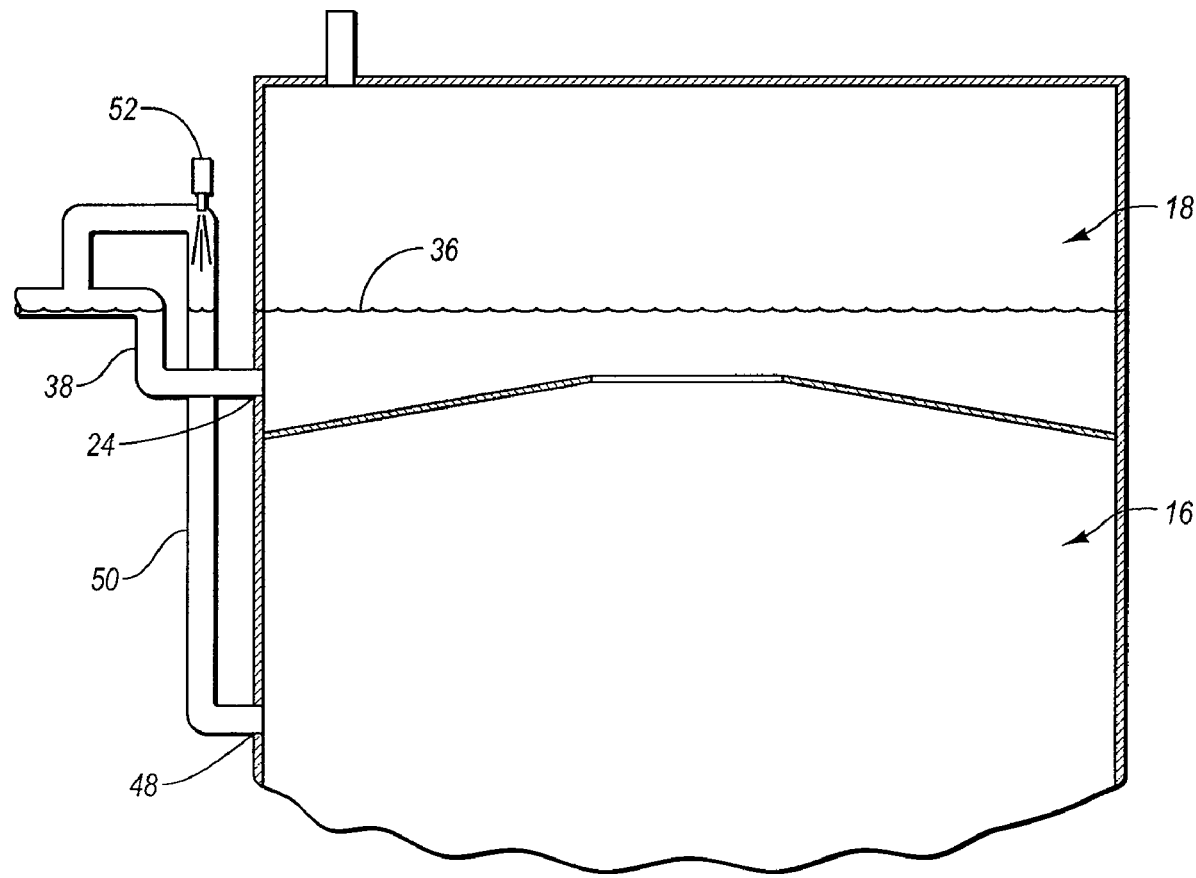
FIG. 6 illustrates an exemplary bioreactor according to the present invention that includes an alternative pressure release mechanism.

FIG. 6 illustrates an alternative mechanism for releasing pressure in the lower chamber of bioreactor 10. In this embodiment, a pressure release outlet 48 is placed in lower chamber 16. The outlet 48 leads to a pressure release line 50. The pressure release line 50 can be ported into the effluent line 38 or alternatively line 50 can be recycled.

In an exemplary embodiment, pressure release line 50 extends above fluid level 36. By extending pressure release line above fluid level 36, pressure release line will be prevented from draining the bioreactor. Once pressure release line is filled with fluid up to fluid level 36, fluid cannot flow out lower chamber 16 through outlet 48 unless sufficient pressure builds to force the fluids in the pressure release line 50 above the fluid level 36. If excess pressure builds in lower chamber 16, the fluid in pressure release line 50 flows into effluent line 38, thereby allowing fluids to exit lower chamber 18 and releasing the excess pressure. Pressure release line 50 is an example of a means for releasing pressure in the lower chamber of the bioreactor. If desired, bioreactor 10 can include a releasable portion in septum 14, in addition to pressure release line 50.

In an exemplary embodiment, pressure release line 50 includes a water jet 52. Water jet 52 can periodically inject water into pressure release line 50 to prevent pressure release line from plugging. By periodically adding a small amount of water to pressure release line 50 a very slow and/or periodic inward flow of water keeps the line clear.

In an exemplary embodiment, pressure release line can also include a flow detector that detects an outward flow of fluids in pressure release line 50. In the event that bioreactor fluids are exiting the reactor through pressure release line 50, the flow detector can cause the loading of digester to be slowed or shut off. In addition, a flow detector can be used to notify personnel that a problem exists.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An upflow bioreactor comprising:
   a vessel having an inlet and an outlet,
   a septum positioned within the vessel and defining a lower chamber and an upper chamber, the septum having an aperture that provides fluid communication between the lower chamber and the upper chamber; and
   a releasable portion of the septum having an open position and a closed position, in which the releasable portion of the septum is configured to move to the open position in response to pressure buildup in the lower chamber and the open position increases the area in fluid communication between the lower chamber and the upper chamber.

2. An upflow bioreactor as in claim 1, in which the releasable portion of the septum comprises a flexible member.

3. An upflow bioreactor as in claim 1, in which the flexible member has a thickness in a range from about 0.15 cm to about 1.5 cm.

4. An upflow bioreactor as in claim 1, in which the aperture has a diameter in a range from about 10 cm to about 2 meters when the releasable portion is in an open position.

5. An upflow bioreactor as in claim 1, in which the aperture has a diameter in a range from about 20 cm to about 100 cm when the releasable portion is in an open position.

6. An upflow bioreactor as in claim 1, in which the releasable portion of the septum comprises a plurality of flexible members positioned over a portion of the aperture in the septum.

7. An upflow bioreactor as in claim 1, further comprising a biomass within the lower chamber, the biomass comprising anaerobic bacteria.

8. An upflow bioreactor as in claim 1 wherein the upper chamber is sealed such that gas produced in the lower chamber can be collected in the upper chamber and introduced into a gas outlet.

9. An upflow bioreactor as in claim 1, further comprising a solids control device within the aperture.

10. An upflow bioreactor as in claim 9, in which the solids control device comprises an auger.

11. An upflow bioreactor as in claim 10, in which a plurality of flexible members covers a portion of the aperture surrounding the solids control device.

12. An upflow bioreactor as in claim 1, in which the inlet is positioned in the lower chamber and the outlet is positioned in the upper chamber such that an upflow is created during operation of the bioreactor.

13. An upflow bioreactor as in claim 11, further comprising a biomass within the lower chamber, the biomass comprising anaerobic bacteria.

14. An upflow bioreactor as in claim 13, wherein the upper chamber is sealed such that gas produced in the lower chamber can be collected in the upper chamber and introduced into a gas outlet.

15. An upflow bioreactor as in claim 13, further comprising a solids control device positioned within the aperture of the septum.

16. An upflow bioreactor comprising:
    a vessel having an inlet and an outlet;
    a septum positioned within the vessel and defining a lower chamber and an upper chamber, the septum having an aperture that provides fluid communication between the lower chamber and the upper chamber;
    a biomass within the lower chamber, the biomass comprising anaerobic bacteria;
    an auger extending through the aperture; and
    at least one flexible member covering a portion of the aperture surrounding the auger.

17. An upflow bioreactor comprising:
    a vessel having an inlet and an outlet;
    positioned within the vessel and defining a lower chamber and an upper chamber, the septum having an aperture that provides fluid communication between the upper chamber and lower chamber;
    a biomass within the lower chamber, the biomass comprising anaerobic bacteria; and
    means for releasing pressure in the lower chamber, wherein the means for releasing pressure in the lower chamber is selectively activated by pressure buildup within the lower chamber, wherein the means for releasing pressure in the lower chamber comprises a releasable portion of the septum having an open position and a closed position, in which the releasable portion of the septum is configured to move to the open position in response to pressure buildup in the lower chamber and the open position increases the fluid communication between the lower chamber and the upper chamber.

18. An upflow bioreactor as in claim 17, in which the releasable portion of the septum comprises a flexible member.

19. An upflow bioreactor as in claim 18, in which the flexible member partially occludes the aperture in the septum.

20. An upflow bioreactor as in claim 19, in which the means for releasing pressure in the lower chamber comprises:
    a tube in fluid communication with the chamber and having an outlet outside the rower chamber;
    a fluid within the tube; and
    a fluid jet configured to add additional fluid to the tube, thereby preventing the tube from plugging.

21. An upflow bioreactor comprising:
    a vessel having an inlet and an outlet;
    a septum positioned within the vessel and defining a lower chamber and an upper chamber, the septum having an aperture that provides fluid communication between the upper chamber and lower chamber;
    a biomass within the lower chamber, the biomass comprising anaerobic bacteria;
    means for releasing pressure in the lower chamber, wherein the means for releasing pressure in the lower chamber is selectively activated by pressure buildup within the lower chamber, wherein the means for releasing pressure in the lower chamber comprises a tube in fluid communication with the lower chamber and having an outlet outside the lower chamber;
    a sensor that is activated by fluid moving out of the tube due to pressure within the lower chamber; and
    circuitry that reduces a loading rate of the vessel upon detecting excess pressure within the lower chamber.

* * * * *